United States Patent
Wollenweber et al.

(10) Patent No.: US 7,542,792 B2
(45) Date of Patent: Jun. 2, 2009

(54) METHODS FOR AUTOMATIC PROTOCOL SELECTION

(75) Inventors: Scott David Wollenweber, Waukesha, WI (US); Charles William Stearns, New Berlin, WI (US); Diane Marie Miesbauer, Hartland, WI (US)

(73) Assignee: General Electric Company, Schenectady, NY (US)

( * ) Notice: Subject to any disclaimer, the term of this patent is extended or adjusted under 35 U.S.C. 154(b) by 934 days.

(21) Appl. No.: 10/858,137

(22) Filed: Jun. 1, 2004

(65) Prior Publication Data

US 2005/0267348 A1    Dec. 1, 2005

(51) Int. Cl.
   *A61B 5/00*   (2006.01)
   *A61B 6/00*   (2006.01)

(52) U.S. Cl. .............. 600/407; 250/370.08; 250/370.09

(58) Field of Classification Search .................. 600/407, 600/425, 428; 250/370.08, 370.09
See application file for complete search history.

(56) References Cited

U.S. PATENT DOCUMENTS

| | | | |
|---|---|---|---|
| 5,241,181 A * | 8/1993 | Mertens et al. ........ | 250/363.03 |
| 5,812,984 A | 9/1998 | Goltra | |
| 5,986,662 A | 11/1999 | Argiro et al. | |
| 6,149,597 A * | 11/2000 | Kamiyama .................. | 600/458 |
| 6,161,757 A | 12/2000 | Morris | |
| 2002/0124054 A1* | 9/2002 | Dorn et al. .................. | 709/217 |
| 2003/0095144 A1 | 5/2003 | Trevino et al. | |
| 2003/0139944 A1 | 7/2003 | Carlsen et al. | |
| 2004/0066909 A1 | 4/2004 | Lonn et al. | |
| 2005/0121505 A1* | 6/2005 | Metz et al. .................. | 235/375 |

OTHER PUBLICATIONS

S.C. Strother, et al., "Measuring PET Scanner Sensitivity...," IEEE Transactions on Nuclear Science, vol. 37, No. 2, Apr. 1990.

\* cited by examiner

*Primary Examiner*—Long V Le
*Assistant Examiner*—Vani Gupta
(74) *Attorney, Agent, or Firm*—The Small Patent Law Group; Dean D. Small

(57) ABSTRACT

A method and apparatus for imaging a patient is provided. The method includes receiving patient information, automatically selecting an imaging protocol based on the received information, and performing an imaging scan of the patient using the automatically selected imaging protocol.

29 Claims, 5 Drawing Sheets

METHODS FOR AUTOMATIC PROTOCOL SELECTION

BACKGROUND OF THE INVENTION

This invention relates generally to medical imaging systems and, more particularly, to automatically selecting a scan protocol for medical imaging systems.

At least some known medical imaging systems include a set-up procedure to prepare the system for a scan of a patient. For example, a trained medical technologist may receive an order from a doctor for a particular type of scan of a region of interest of the patient. To comply with the doctor's order and properly perform the scan, various instructions may be input into a controller of the medical imaging system used to perform the scan. To facilitate such input, several predetermined protocols may be saved in a memory of the medical imaging system and one or more predetermined protocols may be selected such that the instructions and parameters contained in the protocol may be used to control the medical imaging system during the scan. In the specific example of a PET/CT scan, such protocols generally include, for example, emission frame duration, transmission frame duration, number of frames to acquire, frame overlap and choice of image reconstruction method. Predetermined protocols permit the technologist to make a judgment based on the patient size/weight, history, and indication and then select the predetermined protocol that may match the information desired. For example, a lung cancer indication with the purpose of scanning a whole-body looking for malignant metastases may be selected to image from upper-thigh to top of head, whereas, a different indication may be prescribed to image a different portion of the patient or change an emission duration for the frames. However, such protocols are subject to a judgement of the technologist in their selection and the selection may be between two protocols having less than optimal imaging settings for the patient to be scanned.

Additionally, patient-related imaging conditions, such as strict control of imaging time post-injection, injected activity, physiologic uptake, and patient disease state may affect image quality by affecting the dynamic range of imaging of true, random and scatter coincidences.

At least some known imaging systems, for example, a PET imaging system, a rate of prompt (true, scatter, random) coincidence events and random coincidence events are measured per second in real-time. Such rates may be a function of the imaged object size, composition, radiation source distribution, imaging system collimation, detector or scanner axial acceptance angle and radioactivity concentration. As used herein, axial acceptance refers to the maximum out-of-plane angle at which data will be accepted; in a PET detector consisting of stacked rings of detector crystals, axial acceptance corresponds to the maximum accepted ring difference for valid data. Such known imaging systems may set the acceptance angle based upon the dimensionality of the acquisition mode, for example, two dimensional or three dimensional. These fixed values may be based on imaging phantoms or other objects and then analyzing the resultant image quality to determine a reasonable acceptance angle setting. Alternatively, the acceptance angle may be based on results from simulation studies for simple objects, such as uniform cylinders. Such an acceptance angle determination method is not based on the characteristics of either the object currently being imaged or the prompt versus random coincidence rates currently being detected in the imaging system. Various scan parameters, including the axial acceptance angle, coincidence timing window, energy window, and the use (and if used, the configuration) of slice septa are selected by an operator prior to initiation of a patient imaging scan. However, such settings are not based on current conditions during the imaging scan, and as such, the imaging system may not be operating in an optimal manner, as measured by metrics, such as noise-equivalent-count-rate (NECR).

BRIEF DESCRIPTION OF THE INVENTION

In one embodiment, a method and apparatus for imaging a patient is provided. The method includes receiving patient information, automatically selecting an imaging protocol based on the received information, and performing an imaging scan of the patient using the automatically selected imaging protocol.

In another embodiment, an imaging system for imaging a patient is provided. The system includes a first imaging modality unit having a patient bore therethrough, a second imaging modality unit having a patient bore therethrough, a control mechanism communicatively coupled to the first imaging modality unit and the second imaging modality unit to control movement of the first imaging modality unit and the second imaging modality unit, and an automatic protocol selector configured to receive data relating to a patient, parameters relating to a type of scan to be performed, and a selection of a predetermined protocol stored in a database of the control mechanism, automatic protocol selector further configured to determine a scan protocol using at least one of the data relating to the patient, the parameters relating to the type of scan to be performed, and the selected predetermined protocol.

In yet another embodiment, a computer program embodied on a computer readable medium for automatically selecting an imaging protocol using an automatic protocol selector coupled to the imaging system is provided. The imaging system includes a database and a user interface. The program includes a code segment that prompts a user to select a predetermined protocol stored in the database and then displays a function menu on the user interface to prompt the user to input data relating to a type of scan to be performed, prompts the user to input patient data relating to a patient to be scanned, and determines a protocol for the scan based on the predetermined protocol, the type of scan to be performed, and the patient data.

DETAILED DESCRIPTION OF THE INVENTION

Figure 1:
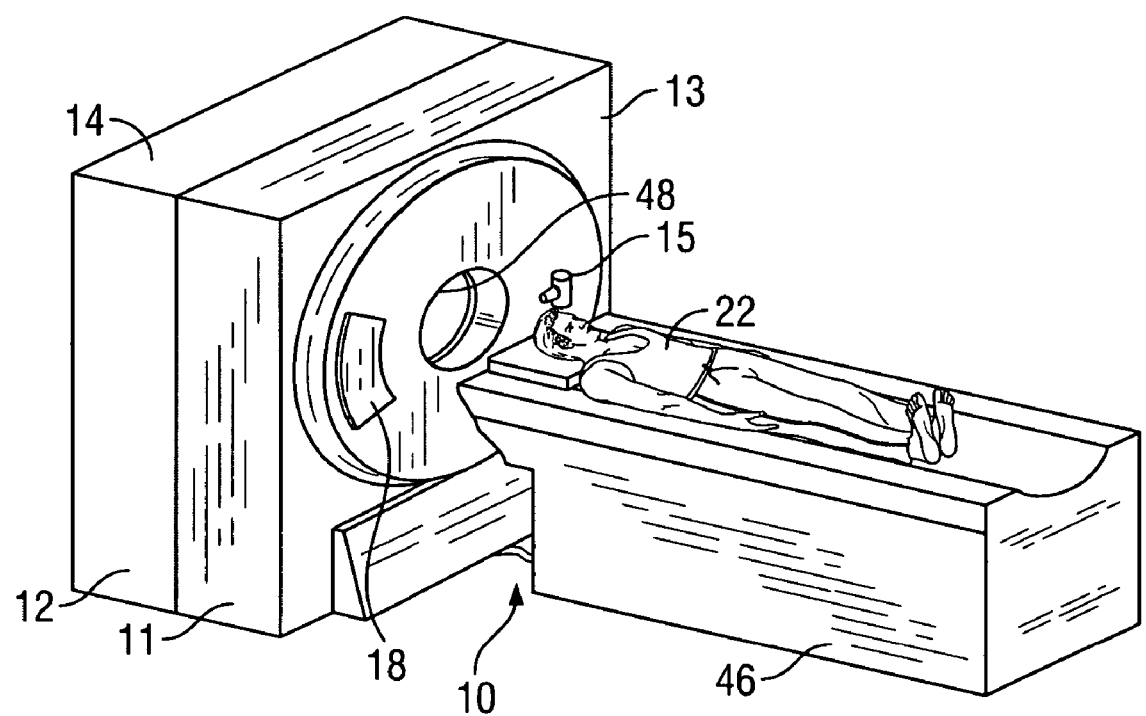
FIG. 1 is a perspective view of an exemplary imaging system.
Figure 2:
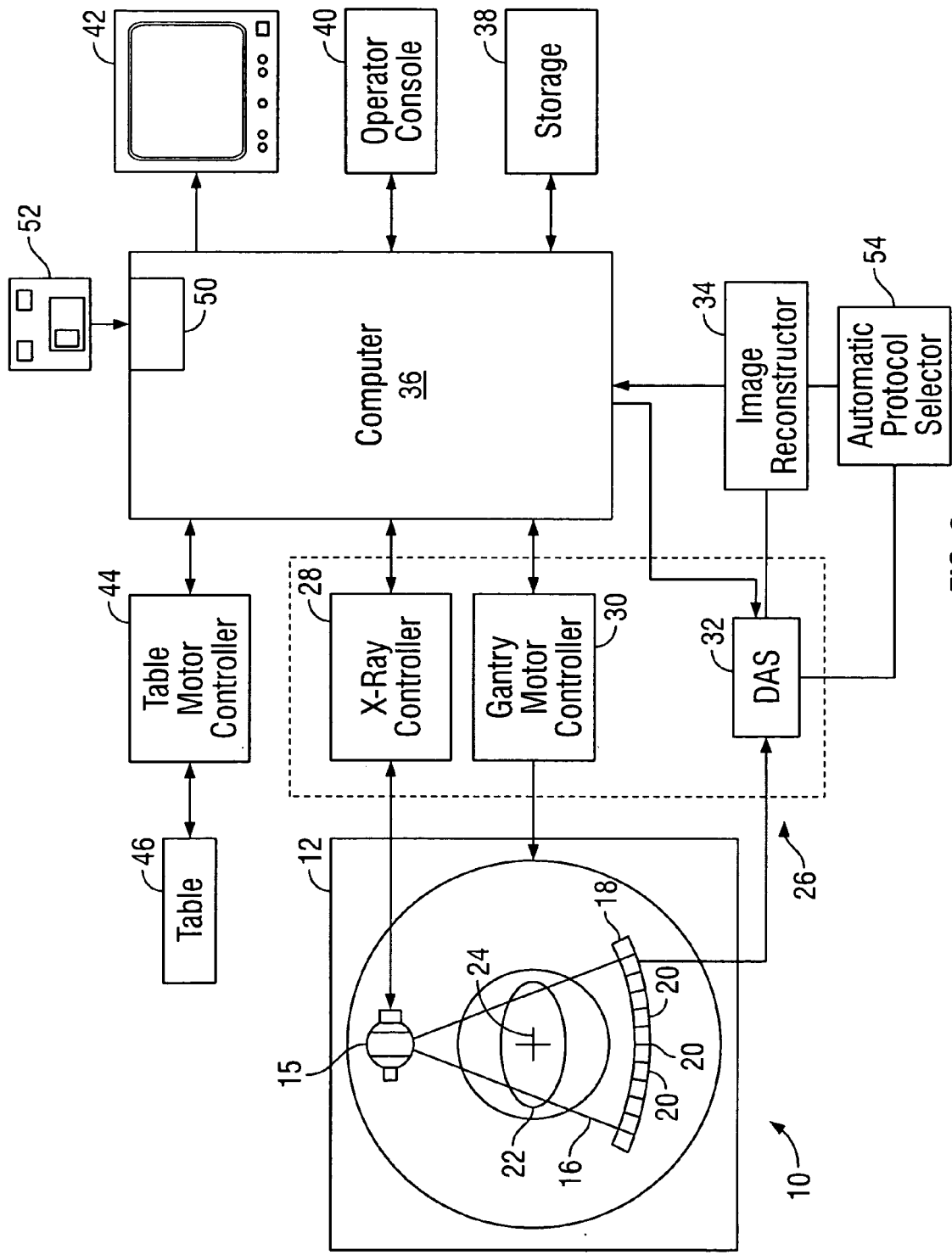
FIG. 2 is a schematic block diagram of the imaging system shown in FIG. 1.

FIG. 1 is a perspective view of an exemplary imaging system 10. FIG. 2 is a schematic block diagram of imaging system 10 (shown in FIG. 1). In the exemplary embodiment, imaging system 10 is a multi-modal imaging system and includes a first modality unit 11 and a second modality unit 12. Modality units 11 and 12 enable system 10 to scan an object, for example, a patient, in a first modality using first modality unit 11 and to scan the object in a second modality using second modality unit 12. System 10 allows for multiple scans in different modalities to facilitate an increased diagnostic capability over single modality systems. In one embodiment, multi-modal imaging system 10 is a Computed Tomography/Positron Emission Tomography (CT/PET) imaging system 10. CT/PET system 10 includes a first gantry 13 associated with first modality unit 11 and a second gantry 14 associated with second modality unit 12. In alternative embodiments, modalities other than CT and PET may be employed with imaging system 10. Gantry 13 includes first modality unit 11 that has an x-ray source 15 that projects a beam of x-rays 16 toward a detector array 18 on the opposite side of gantry 13. Detector array 18 is formed by a plurality of detector rows (not shown) including a plurality of detector elements 20 that together sense the projected x-rays that pass through an object, such as a patient 22. Each detector element 20 produces an electrical signal that represents the intensity of an impinging x-ray beam and therefore, allows estimation of the attenuation of the beam as it passes through object or patient 22.

During a scan, to acquire x-ray projection data, gantry 13 and the components mounted thereon rotate about an examination axis 24. FIG. 2 shows only a single row of detector elements 20 (i.e., a detector row). However, a detector array 18 may be configured as a multislice detector array having a plurality of parallel detector rows of detector elements 20 such that projection data corresponding to a plurality of slices can be acquired simultaneously during a scan. To acquire emission data, gantry 14 rotates one or more gamma cameras (not shown) about examination axis 24. Gantry 14 may be configured for continuous rotation during an imaging scan and/or for intermittent rotation between imaging frames.

The rotation of gantries 13 and 14, and the operation of x-ray source 15 are controlled by a control mechanism 26 of CT/PET system 10. Control mechanism 26 includes an x-ray controller 28 that provides power and timing signals to x-ray source 15 and a gantry motor controller 30 that controls the rotational speed and position of gantry 13 and gantry 14. A data acquisition system (DAS) 32 of control mechanism 26 samples data from detector elements 20 and the gamma cameras and conditions the data for subsequent processing. An image reconstructor 34 receives sampled and digitized x-ray data and emission data from DAS 32 and performs high-speed image reconstruction. The reconstructed image is transmitted as an input to a computer 36 which stores the image in a storage device 38.

Computer 36 also receives commands and scanning parameters from an operator via console 40 that has an input device, such as, keyboard. An associated display 42 allows the operator to observe the reconstructed image and other data from computer 36. The operator supplied commands and parameters are used by computer 36 to provide control signals and information to DAS 32, x-ray controller 28 and gantry motor controller 30. In addition, computer 36 operates a table motor controller 44 which controls a motorized table 46 to position patient 22 in gantry 13 and 14. Specifically, table 46 moves portions of patient 22 through gantry opening 48.

In one embodiment, computer 36 includes a read/write device 50, for example, a floppy disk drive, CD-ROM drive, DVD drive, magnetic optical disk (MOD) device, or any other digital device including a network connecting device such as an Ethernet device for reading instructions and/or data from a computer-readable medium 52, such as a floppy disk, a CD-ROM, a DVD or an other digital source such as a network or the Internet, as well as yet to be developed digital means. In another embodiment, computer 36 executes instructions stored in firmware (not shown). Computer 36 is programmed to perform functions as described herein, and as used herein, the term computer is not limited to integrated circuits referred to in the art as computers, but broadly refers to computers, processors, microcontrollers, microcomputers, programmable logic controllers, application specific integrated circuits, and other programmable circuits, and these terms are used interchangeably herein. CT/PET system 10 also includes a plurality of PET detectors (not shown) including a plurality of detector elements. The PET detectors and detector array 18 both detect radiation and are both referred to herein as radiation detectors.

An automatic protocol selector 54 is communicatively coupled to DAS 32 and image reconstructor 34 to transmit settings and parameters for use by DAS 32 and image reconstructor 34 during a scan and/or image reconstruction and image review. Although automatic protocol selector 54 is illustrated as a separate component, it should be understood that that functions performed by automatic protocol selector 54 may be incorporated into functions performed by, for example computer 36. Accordingly automatic protocol selector 54 may be embodied in a software code segment executing on a multifunctional processor or may embodied in a combination of hardware and software.

Additionally, although described in a medical setting, it is contemplated that the embodiments of the invention may be implemented in connection with other imaging systems including industrial CT systems such as, for example, but not limited to, a baggage scanning CT system typically used in a transportation center such as, for example, but not limited to, an airport or a rail station.

Figure 3:
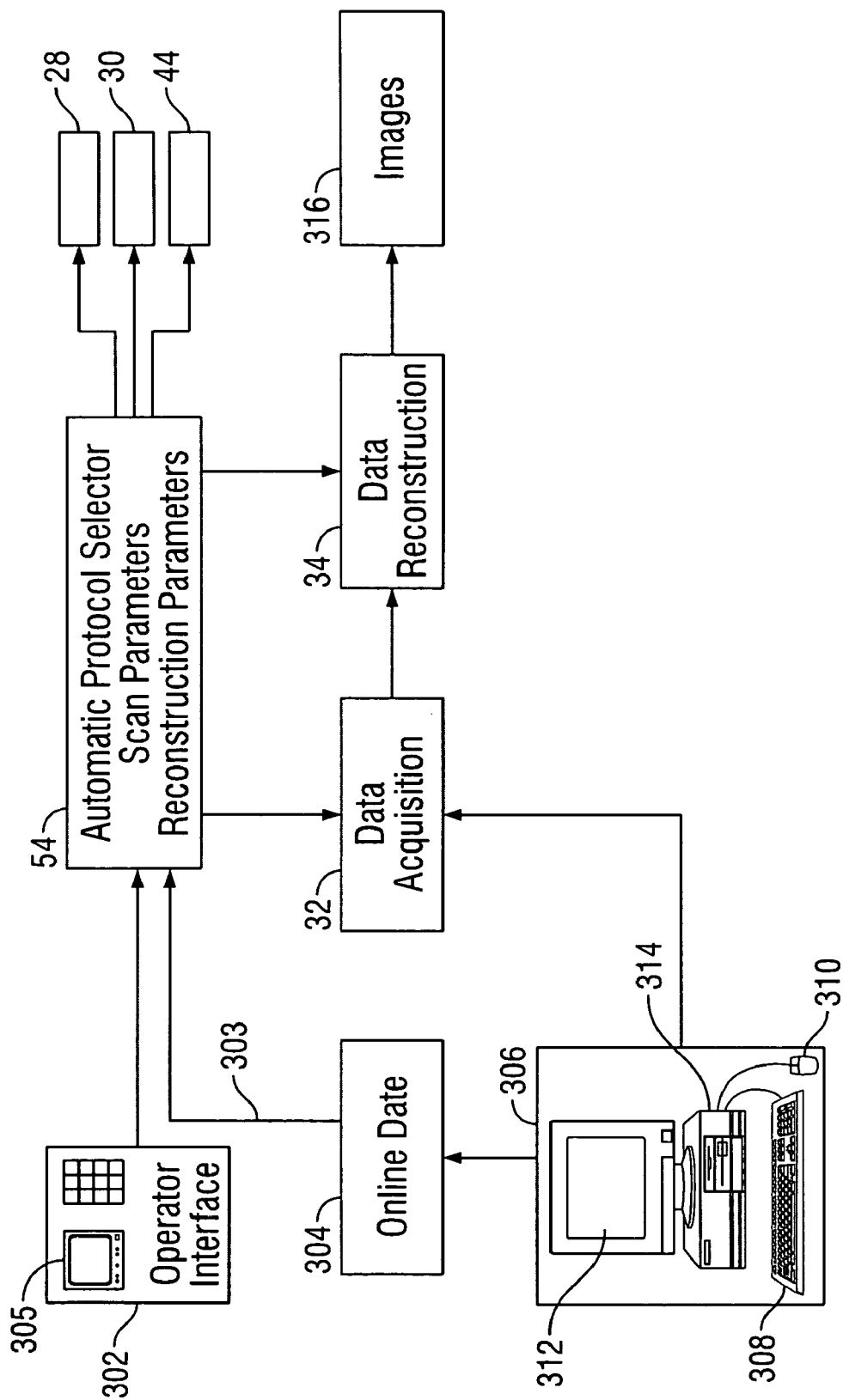
FIG. 3 is a block diagram of the automatic protocol selector shown in FIG. 2 in accordance with an exemplary embodiment of the present invention.

FIG. 3 is a block diagram of an exemplary embodiment of automatic protocol selector 54 (shown in FIG. 2). Automatic protocol selector 54 is configured to receive one or more inputs from an operator interface 302. The inputs may be received, for example, but not limited to, via a keyboard, a mouse, a touch-screen, and by voice commands. Automatic protocol selector 54 is also configured to receive data from an on-line data source 304, such as a database accessible through a network 303, for example, the Internet, a WAN, LAN, a picture archiving and communications system (PACS), and a digital imaging and communications in medicine (DICOM) system. In addition to receiving digitized images, for example, pixel data, the received data, such as a DICOM object, may also include attribute information. For example, the attribute information may include patient attributes, such as, but not limited to a patient name, a patient height, a patient weight, and a patient identification number; exam attributes, such as, but not limited to exam description and exam date; series attributes such as, but not limited to modality type and series date; and image attributes such as, but not limited to image type and numbers of rows and columns. In the exemplary embodiment, each attribute has a name, a value representation and a tag. A tag is a number unique to the attribute and is used to identify the attribute. Additionally, on-line data source 304 may receive patient information directly from a patient through a patient interface 306 such as a keyboard 308, a mouse 310, a touch screen display 312 or other input device, such as a patient data magnetic stripe card, intelligent data card, or a flash memory device through a connector or reader 314. The patient entered information may be transmitted directly to DAS 32 and may be transmitted to on-line data source 304.

Automatic protocol selector 54 receives patient data from the patient through patient interface 306 and on-line patient data through on-line data source 304 that may include archive data relating to, for example, previous imaging scans, treatments, medications, and patient vitals. Automatic protocol selector 54 also receives patient and/or scan data through operator interface 302. Automatic protocol selector 54 then facilitates an imaging protocol selection through automatic selection of a pre-programmed protocol using the patient information entered through patient interface 306, received through on-line data source 304 from the hospital information system, and/or the indication of the PET scan from a doctor and entered through operator interface 302. For example, operator interface may include a display 305 wherein graphical icons may be displayed to select whether the protocol is for abdomen, chest, head-thigh, head-foot, whole body, and selection of a landmark. Also, predetermined number selection ranges, such as, a fraction and a weight bar may be parameterized such that a specific facility may customize automatic protocol selector 54 to a specific patient population.

Automatic protocol selector 54 then automatically selects, using the entered data, an optimal protocol from a plurality of pre-programmed protocols that include parameters for various intended uses of imaging system 10. The selection may then be approved by the operator or modified through selection of a different one of the plurality of protocols, or by editing any of the parameters through operator interface 302. When a protocol is approved by the operator, parameters controlling the image scan may be transmitted to controllers 28, 30, and 44. Parameters controlling the acquisition of the scan images may be transmitted to DAS 32, and parameters controlling the reconstruction of the scan images may be transmitted to image reconstructor 34. Controlling scan parameters and reconstruction parameters using automatic protocol selector 54 facilitates automatic control of image data acquisition and automatic control of reconstruction of images 316. Parameters transmitted to DAS 32 from automatic protocol selector 54 may define, for example, but not limited to, emission frame duration, transmission frame duration, number of frames to acquire, frame overlap, energy thresholds for accepted events, and the use and configuration of slice collimation. Parameters transmitted to image reconstructor 34 from automatic protocol selector 54 may define, for example, but not limited to, the image reconstruction method to be applied to the data, the parameters used in that reconstruction method, and filters applied to the data before, during or after the reconstruction process.

Figure 4:
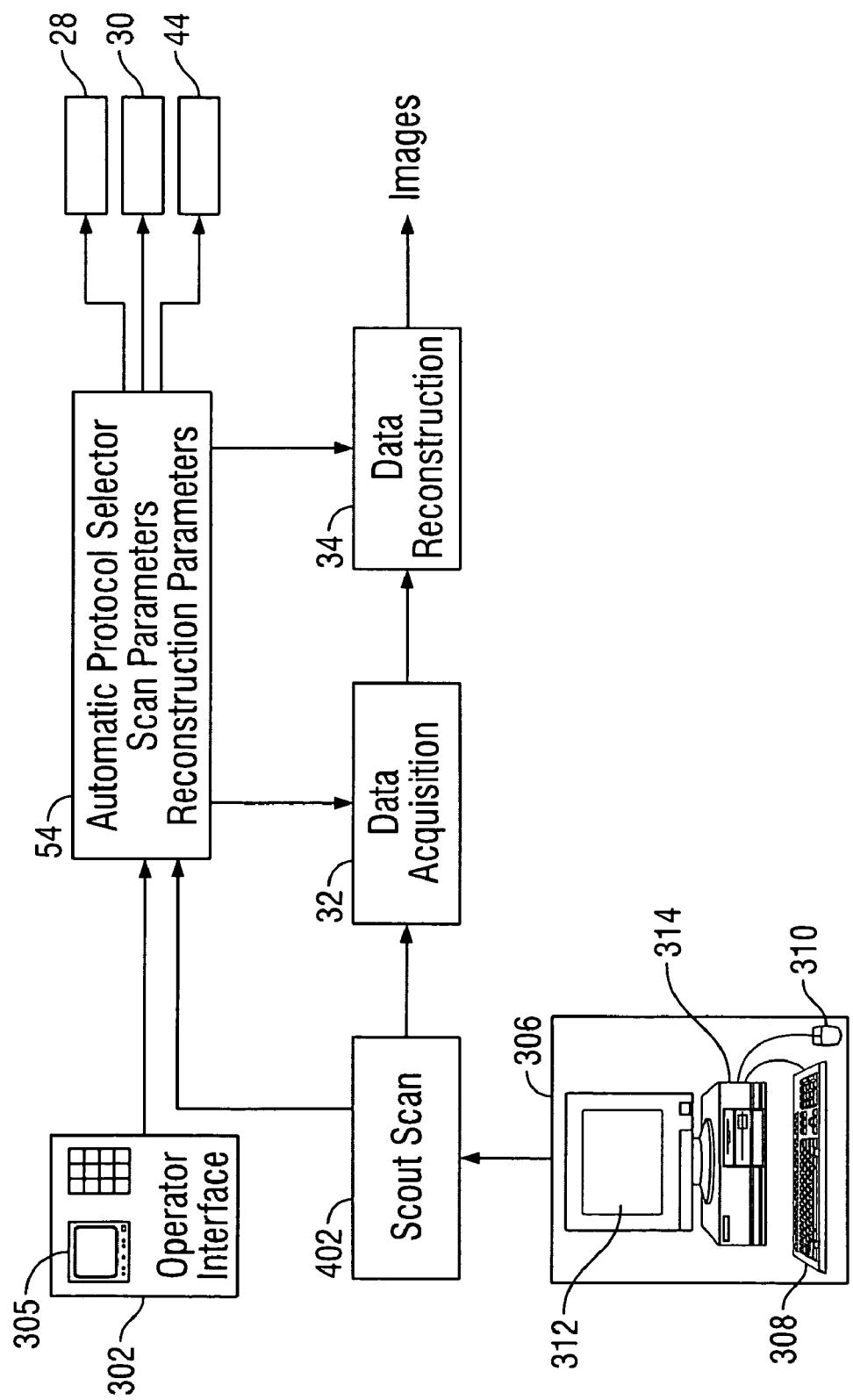
FIG. 4 is a block diagram of another exemplary embodiment of the automatic protocol selector shown in FIG. 2.

FIG. 4 is a block diagram of another exemplary embodiment of automatic protocol selector 54 (shown in FIG. 2) for a combined CT/PET scanner. In this exemplary embodiment, automatic protocol selector 54 includes an input from a preliminary, or scout, scan 402, for example, a first modality scout scan, such as a CT scout scan, and/or a second modality scout scan, such as a PET scout scan. Scout scan 402 may be used concurrently with on-line data source 304, or may be used independently of on-line data source 304.

During operation, input parameters are entered into system 10 from patient interface 306, on-line data source 304, and operator interface 302. System 10 performs a scout scan 402 of patient 22 wherein scout scan 402 is a relatively short time duration real-time scan of patient 22 performed between the detector arrival time at the image frame and the scan data acquisition at that frame. The acquired prompt and random coincidence event rates from scout scan 402 may be transmitted to automatic protocol selector 54 wherein an optimal axial acceptance angle for the current conditions may be calculated based upon the input patient parameters, the scout scan input parameters, and the acquired prompt and random coincidence event rates. The calculated axial acceptance angle is set by system 10 and the final frame scan is initiated.

In one embodiment of this procedure to calculate the optimal axial acceptance for the PET acquisition, the PET scout scan may be acquired with full acceptance the maximum axial acceptance permitted. A noise equivalent count rate (NECR) versus acceptance angle function may be generated to permit selection of an optimal NECR to be used during the final frame scan when the image frame data is acquired. Accordingly, the optimal NECR setting selection is based on current conditions of patient 22 and system 10. The peak of the NECR versus acceptance angle function may be defined as the acceptance angle associated with the largest NECR.

NECR may be defined as the square of the signal-to-noise ratio and may be expressed as:

$$NECR = \frac{Signal^2}{\sigma^2} = \frac{T^2}{T+S+kR},$$

Where:
T=True coincidence events
S=Scatter events
R=Random events
k accounts for the method of random events correction, wherein
 k=1 for random from singles events
 k=2 for unprocessed delayed event subtraction (real-time or from separate delayed sinogram)

In an alternative embodiment, the acceptance angle may be selected such that it does not correspond to the peak of the NECR versus acceptance angle function but rather corresponds to an NECR value that is also based on the half-life of the radiopharmaceutical tracer used when performing the scan and a shape of the generated NECR function to optimize the acceptance angle based on the decay of the radiopharmaceutical during the duration of the image frame scan, which may take several minutes, for example, fifteen to thirty minutes, to complete. In another alternative embodiment, a complete set of acceptance angles are measured during an acquisition mode and if the acquisition mode is a 2D mode the data may be rebinned based on a determined NECR versus acceptance angle function. If the acquisition mode is a 3D mode, data from a portion of the angles may be discarded during image reconstruction. In a further alternative embodiment, an acquisition timing, a gamma energy window, and the use and configuration of slice septa in the acquisition are modified together with acceptance angle to optimize the NECR value of the final frame scan.

Figure 5:
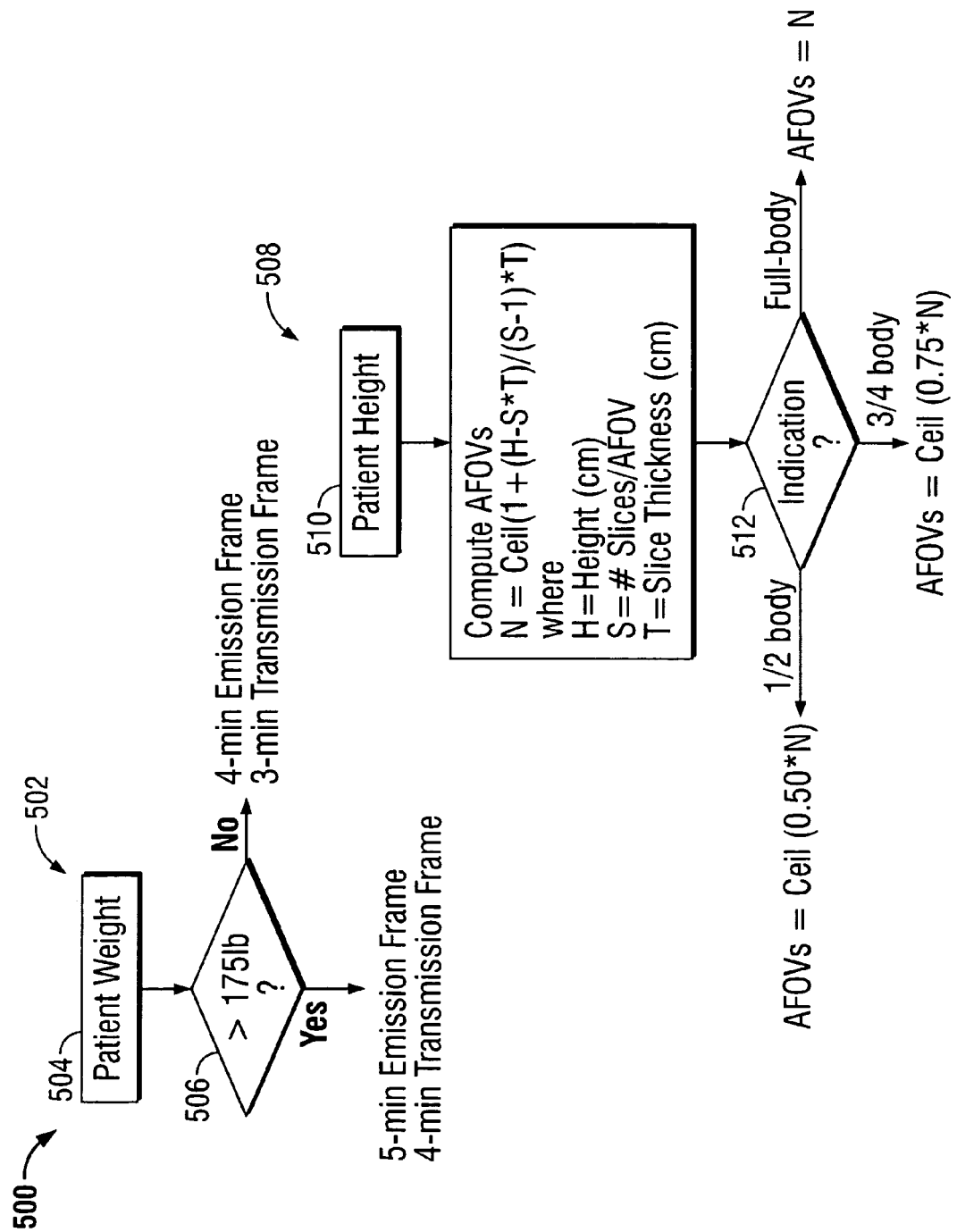
FIG. 5 is a flow diagram of an automatic protocol selection method in accordance with an exemplary embodiment of the present invention that may be used by the automatic protocol selector shown in FIG. 2.

FIG. 5 is a flow diagram 500 of an exemplary automatic protocol selection method based on patient 22 characteristics that may be used in automatic protocol selector 54 (shown in FIG. 2-4). In a first selection process 502, a patient weight 504 may be compared at 506 to a cutoff weight, for example, 175 pounds to determine an emission frame time duration and/or a transmission frame time duration. Patient weight 504 may be determined from an input to operator interface 302, patient interface 306 and/or on-line data source 304. The value of the cutoff weight may be parameterized such that the value is customized for a particular facility where system 10 may be used, for example, for use in a children's hospital a cutoff weight of less than 175 may be set as a default cutoff weight. In an alternative embodiment, the comparison may be performed continuously through the use of an emission time versus weight function and/or a transmission time versus weight function that may be used to determine a more specific emission time and transmission time for the entered weight. In another alternative embodiment, a lookup table is used to correlate the patient weight to an optimal emission time and transmission time for that weight.

In a second selection process 508, a patient height 510, a number of image slices per axial field of view (AFOV), a slice thickness, and a scan indication 512 may be used to determine an AFOV of a scan. As shown in the equation in FIG. 5, "N" is an integer value representing the number of fields-of-view to be imaged in the whole-body imaging study and "ceil" is a ceiling function. Patient height 510 may be entered thorough, for example, patient interface 306, operator interface 302, and on-line data source 304. The number of image slices per AFOV, the slice thickness, and scan indication 512 may be entered through, for example, operator interface 302, and on-line data source 304. Other parameters may similarly be used to provide input to automatic protocol selector 54, such as, for example, patient age, gender, body type, body mass index (BMI), chest measurement, and abdomen measurement.

Patient weight 504 and patient height 510, in addition to other patient parameters may then be used by automatic protocol selector 54 to determine optimal settings for the PET and CT scan parameters and image reconstruction parameters automatically, subject to approval by the user.

The above-described automatic protocol selector system is cost-effective and highly reliable means for determining a parameters that control the acquisition of image data and the reconstruction of the images. Each system is configured to use patient data and to optimize the imaging system NECR based on a scout scan of relevant count rates, estimation of NECR for changes in the parameters, and change of the system scan parameters for the scan/frame prior to final initiation of the acquisition. Accordingly, the automatic protocol selector system facilitates the control of imaging data acquisition and reconstruction, in a cost-effective and reliable manner.

Exemplary embodiments of automatic protocol selector system components are described above in detail. The components are not limited to the specific embodiments described herein, but rather, components of each system may be utilized independently and separately from other components described herein. Each automatic protocol selector system component can also be used in combination with other automatic protocol selector system components.

While the invention has been described in terms of various specific embodiments, those skilled in the art will recognize that the invention can be practiced with modification within the spirit and scope of the claims.

What is claimed is:

1. A method of imaging a patient, said method comprising:
receiving patient information;
measuring prompt and random coincidence rates in real time using a scout scan performed by a medical imaging system;
automatically selecting an imaging protocol based on the received information and the measured prompt and random coincidence rates; and
performing, with the medical imaging system, an imaging scan of the patient using the automatically selected imaging protocol.

2. A method in accordance with claim 1 wherein receiving patient information comprises prompting a user to enter the patient information using a user interface.

3. A method in accordance with claim 1 wherein receiving patient information comprises receiving at least one of a height and a weight of the patient.

4. A method in accordance with claim 1 wherein receiving patient information comprises receiving the patient information from a database accessible to the imaging system through a data network.

5. A method in accordance with claim 4 wherein receiving patient information comprises receiving the patient information from a DICOM system.

6. A method in accordance with claim 1 wherein performing an imaging scan of the patient using the automatically selected imaging protocol comprises determining at least one of an emission frame and a transmission frame.

7. A method in accordance with claim 1 wherein performing an imaging scan of the patient using the automatically selected imaging protocol comprises determining an axial field of view (N) using, $$N=\mathrm{Ceil}\,(1+(H-(S*T))/(S-1)*T), \text{ where}$$

N is an integer value representing the number of axial fields-of-view to be imaged;
Ceil is a ceiling function;
H=a patient height in cm,
S=a number of slices per AFOV, and
T=a slice thickness.

8. A method in accordance with claim 1 wherein measuring prompt and random coincidence rates in real time using a scout scan comprises performing a scan of relatively short time duration using full acceptance angles.

9. A method in accordance with claim 1 wherein measuring prompt and random coincidence rates in real time using a scout scan comprises performing a scan of less than ten seconds using full acceptance angles.

10. A method in accordance with claim 9 further comprising generating a noise-equivalent-count-rate (NECR) versus acceptance angle curve using the measured prompt and random coincidence rates.

11. A method in accordance with claim 10 further comprising determining an optimal acceptance angle for performing the imaging scan using the NECR versus acceptance angle curve.

12. A method in accordance with claim 1 wherein performing an imaging scan of the patient using the automatically selected imaging protocol comprises modifying, in real time, at least one of an axial acceptance angle, a coincidence timing window, an energy window, a use and configuration of slice septa of the scan using the measured prompt and random coincidence rates.

13. A method in accordance with claim 1 wherein performing an imaging scan of the patient using the automatically selected imaging protocol comprises estimating a scatter coincidence rate using the prompt and the random coincidence rates.

14. A method in accordance with claim 13 wherein performing an imaging scan of the patient using the automatically selected imaging protocol comprises modifying, in real time, at least one of an axial acceptance angle, a coincidence timing window, an energy window, the use and configuration of slice septa of the scan using the estimated scatter coincidence rate and the personal information.

15. A method of imaging a patient using a medical imaging scanner, said method comprising:
receiving information relative to a patient's size and density;
automatically selecting an imaging protocol to operate a medical imaging system, the imaging protocol based on the received information wherein the protocol includes at least one of an axial acceptance angle, a coincidence timing window, an energy window, a "d-ness" of the scan;

acquiring a prompt coincidence rate and a random coincidence rate at an imaging frame;

modifying a imaging protocol using the received information, the prompt coincidence rate, and the random coincidence rate; and performing with the medical imaging system an imaging scan of the patient using the modified imaging protocol.

16. A method in accordance with claim 15 wherein modifying a imaging protocol using the received information comprises modifying the axial acceptance angle to an optimal acceptance angle, using the patient size and the acquired prompt coincidence rate and the random coincidence rate.

17. A method in accordance with 15 wherein acquiring a prompt coincidence rate and a random coincidence rate at an imaging frame comprises acquiring a prompt coincidence rate and a random coincidence rate using a full acceptance angle setting.

18. A method in accordance with claim 15 further comprising generating a function curve relating an NECR for the scanner at a plurality of scanner acceptance angles.

19. A method in accordance with claim 18 further comprising selecting an acceptance angle corresponding to a peak NECR of the function curve to perform the imaging scan.

20. A method in accordance with claim 18 further comprising selecting an acceptance angle corresponding to a NECR value peak of the function curve to perform the imaging scan.

21. An imaging system for imaging a patient, said system comprising:
  a first imaging modality unit having a patient bore therethrough;
  a second imaging modality unit having a patient bore therethrough;
  a control mechanism configured to measure prompt and random coincidence rates in real time using a scout scan, and communicatively coupled to said first imaging modality unit and said second imaging modality unit to control movement of said first imaging modality unit and said second imaging modality unit;
  an automatic protocol selector configured to receive data relating to a patient, parameters relating to a type of scan to be performed, and a selection of a predetermined protocol stored in a database of said control mechanism, said automatic protocol selector further configured to determine a scan protocol using at least one of the data relating to the patient, the parameters relating to the type of scan to be performed, and the selected predetermined protocol and the measured prompt and random coincidence rates.

22. An imaging system in accordance with claim 21 further configured to:
  rotate at least one of said first imaging modality unit and said second imaging modality unit to a image frame position;
  acquire prompt and random coincidence event rates during a scout scan;
  determine an axial acceptance angle that facilitates a maximizing a noise-equivalent-count-rate that is based on the acquired prompt and random coincidence event rates; and
  perform an image data acquisition at said image frame position.

23. An imaging system in accordance with claim 21 wherein said first imaging modality unit is a PET imaging system and said second imaging modality unit is a CT imaging system.

24. A computer program embodied on a computer readable medium for automatically selecting an imaging protocol using an automatic protocol selector coupled to said imaging system, said imaging system including a database and a user interface, said program comprising a code segment that prompts a user to select a predetermined protocol stored in said database and then:
  displays a function menu on said user interface to prompt the user to input data relating to a type of scan to be performed;
  prompts the user to input patient data relating to a patient to be scanned;
  measures prompt and random coincidence rates in real time using a scout scan; and
  determines a protocol for the scan based on the predetermined protocol, the type of scan to be performed, the patient data, and the prompt and random coincidence rates.

25. A computer program in accordance with claim 24 further comprising a code segment configured to prompt a user to accept the determined protocol.

26. A computer program in accordance with claim 24 further comprising a code segment configured to transmit at least one parameter of the determined protocol to a data acquisition system.

27. A computer program in accordance with claim 24 further comprising a code segment configured to transmit at least one parameter of the determined protocol to an image reconstructor.

28. A computer program in accordance with claim 24 further comprising a code segment configured to transmit control signals to at least one of an x-ray controller, that provides power and timing signals to an x-ray source, a gantry motor controller, and a table motor controller.

29. A computer program in accordance with claim 24 wherein said first imaging modality unit is a PET imaging system and said second imaging modality unit is a CT imaging system.

* * * * *